United States Patent
Elmalak et al.

(10) Patent No.: US 12,369,947 B2
(45) Date of Patent: Jul. 29, 2025

(54) SELF-HEALING BALLOONS

(71) Applicant: STRYKER EUROPEAN OPERATIONS LIMITED, Carrigtwohill (IE)

(72) Inventors: Omar Elmalak, Jat (IL); Moran Haim-Zada, Caesarea (IL); Abraham J. Domb, Caesarea (IL)

(73) Assignee: STRYKER EUROPEAN OPERATIONS LIMITED, Carrigtwohill (IE)

( * ) Notice: Subject to any disclaimer, the term of this patent is extended or adjusted under 35 U.S.C. 154(b) by 1456 days.

(21) Appl. No.: 16/635,623

(22) PCT Filed: Jul. 31, 2018

(86) PCT No.: PCT/IB2018/055751
§ 371 (c)(1),
(2) Date: Jan. 31, 2020

(87) PCT Pub. No.: WO2019/025982
PCT Pub. Date: Feb. 7, 2019

(65) Prior Publication Data
US 2021/0030441 A1    Feb. 4, 2021

Related U.S. Application Data

(60) Provisional application No. 62/540,869, filed on Aug. 3, 2017.

(51) Int. Cl.
| | | |
|---|---|---|
| *A61B 17/56* | (2006.01) | |
| *A61L 27/04* | (2006.01) | |
| *A61L 27/20* | (2006.01) | |
| *A61L 27/22* | (2006.01) | |
| *A61L 27/52* | (2006.01) | |
| *A61L 27/58* | (2006.01) | |
| *A61B 17/00* | (2006.01) | |

(52) U.S. Cl.
CPC .......... *A61B 17/562* (2013.01); *A61L 27/042* (2013.01); *A61L 27/047* (2013.01); *A61L 27/20* (2013.01); *A61L 27/22* (2013.01); *A61L 27/227* (2013.01); *A61L 27/52* (2013.01); *A61L 27/58* (2013.01); *A61B 2017/00004* (2013.01); *A61L 2430/24* (2013.01); *A61L 2430/36* (2013.01)

(58) Field of Classification Search
CPC .................................................. A61B 17/562
See application file for complete search history.

(56) References Cited

U.S. PATENT DOCUMENTS

| | | | |
|---|---|---|---|
| 8,753,390 B2 | 6/2014 | Shohat | |
| 8,894,713 B2 | 11/2014 | Shohat et al. | |
| 9,623,146 B2 * | 4/2017 | Lamberti | .................. A61P 7/00 |
| 2006/0159823 A1 | 7/2006 | Melvik et al. | |
| 2007/0255394 A1 * | 11/2007 | Ryan | ..................... A61F 2/2418 |
| | | | 623/1.24 |
| 2009/0234457 A1 * | 9/2009 | Lotz | ........................ A61L 27/52 |
| | | | 623/1.15 |
| 2014/0271903 A1 | 9/2014 | Sutariya et al. | |

FOREIGN PATENT DOCUMENTS

| | | | | |
|---|---|---|---|---|
| WO | 2008111073 A2 | 9/2008 | | |
| WO | WO-2008139473 A2 * | 11/2008 | .......... | A61L 29/146 |
| WO | 2010097724 A1 | 9/2010 | | |
| WO | 2012017438 A1 | 2/2012 | | |
| WO | 2013057566 A2 | 4/2013 | | |

OTHER PUBLICATIONS

Bioscience GMBH, Technologies, Jun. 30, 2017 (retrieved on Oct. 23, 2018). Retrieved from the Internet: <URL: https://web.archive.org/web/20170630230449/https://www.bio-science.org/technology/>.
International Search Report for PCT/IB2018/055751 mailed Nov. 19, 2018.
Majd SE et al., "Both Hyaluronan and Collagen Type II Keep Proteoglycan 4 (Lubricin) at the Cartilage Surface in a Condition That Provides Low Friction during Boundary Lubrication," Langmuir Dec. 2014. 9, 30 (48), 14566-14572.
Bae KH, Wang LS, Kurisawa M. Injectable biodegradable hydrogels: progress and challenges. Journal of Materials Chemistry B. 2013;1(40):5371-88.
Dou QQ, Liow SS, Ye E, Lakshminarayanan R, Loh XJ. Biodegradable thermogelling polymers: working towards clinical applications. Advanced healthcare materials. Jul. 2014;3(7):977-88.
Kondiah PJ, Choonara YE, Kondiah PP, Marimuthu T, Kumar P, Du Toit LC, Pillay V. A review of injectable polymeric hydrogel systems for application in bone tissue engineering. Molecules. Nov. 2016;21(11):1580.

* cited by examiner

*Primary Examiner* — Andrew S Rosenthal
*Assistant Examiner* — Danielle Kim
(74) *Attorney, Agent, or Firm* — Foley & Lardner LLP

(57) ABSTRACT

A balloon implantation kit includes an inflatable biodegradable balloon configured to be implanted in a human body and a hydrogel composition. In some cases, the hydrogel composition is provided in a container configured to be introduced into the biodegradable balloon. For some applications, the biodegradable balloon includes a joint spacer for treatment of a joint of a human subject, such as a subacromial spacer, a glenohumeral spacer, or a spacer for another joint, such as a knee, hip, ankle, or hand (e.g., CMC1) joint. In these applications, the biodegradable balloon is configured to be inserted into a space of a joint of the human body, and is shaped to provide mechanical support to the joint until the biodegradable balloon resorbs into the human body. For other applications, the biodegradable balloon includes a soft tissue spacer.

20 Claims, 6 Drawing Sheets

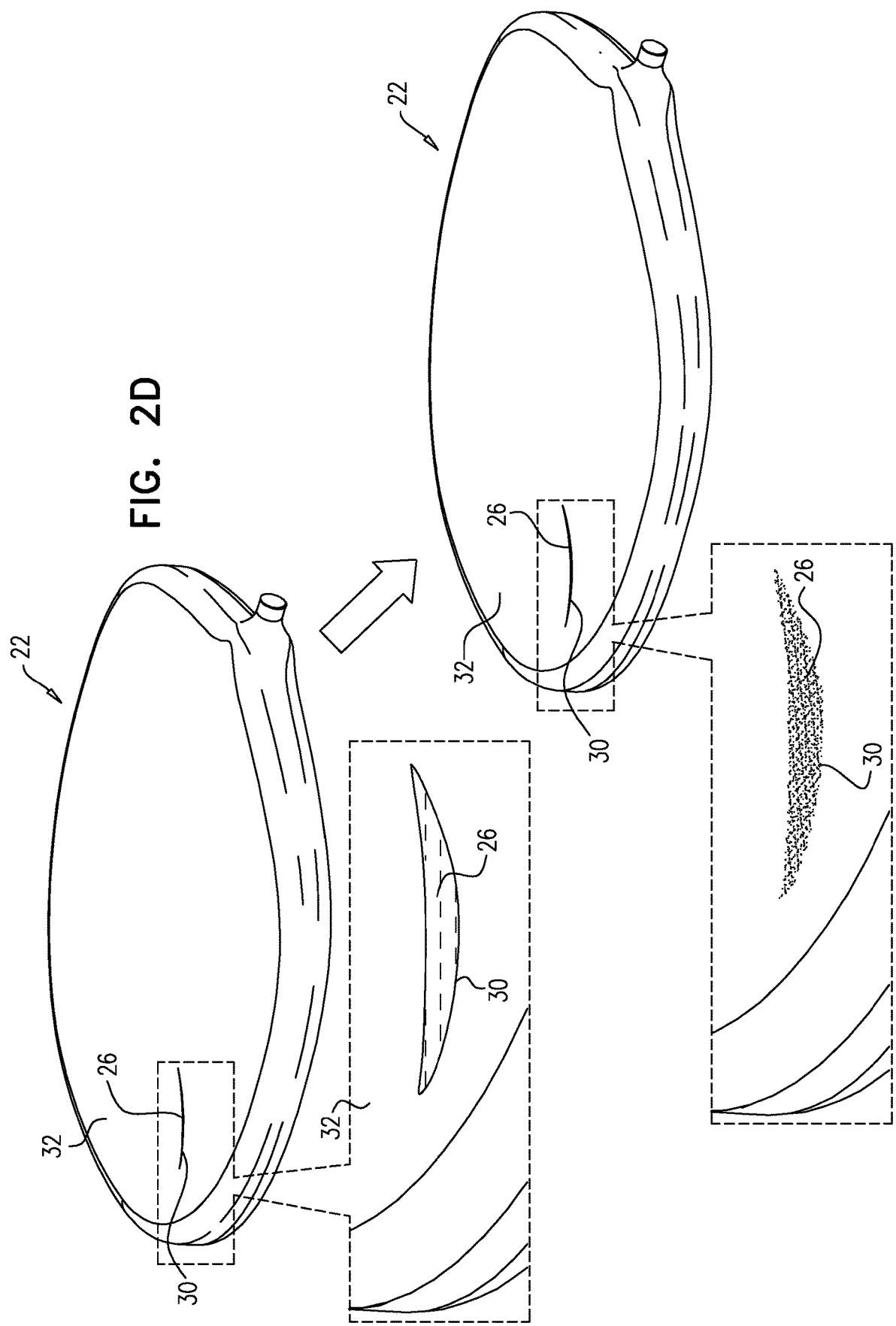

SELF-HEALING BALLOONS

CROSS-REFERENCE TO RELATED APPLICATION

The present application is a national phase entry under 35 U.S.C. § 371 of International Application No. PCT/IB2018/055751, filed Jul. 31, 2018, which claims the benefit of U.S. Provisional Application Ser. No. 62/540,869, filed Aug. 3, 2017, the contents of which are incorporated herein by reference in its entirety.

TECHNICAL FIELD

The present invention relates generally to inflatable balloons, and specifically to inflatable balloons for implantation in a human body.

BACKGROUND

Inflatable members, such as balloons, are sometimes implanted in a human body, e.g., a joint, such as the shoulder joint, the prostate, or the stomach. Through repeated strenuous motion, sensitive soft tissues often suffer wear and tear injuries from repeatedly rubbing against one another and/or hard tissues, such as bone. Tears of rotator cuff tendons and articular capsule disintegration are examples of this type of injury. In addition, these tissues can be adversely affected by inflammation, infection, disease and/or genetic predispositions which lead to degeneration of these tissues. Inflatable balloons may be implanted at such a site to reduce injury to the site.

There are four major biodegradation mechanisms for polymers used in biomedical devices: hydrolysis (reaction with water in tissues), oxidation (due to oxidants produced by tissues), enzymatic degradation, and physical erosion. The degradation or erosion mechanisms include cleavage of bonds resulting in the reduction of molar mass and solubilization of the polymers in biological fluids which result in reduction of mechanical properties followed by mass loss as a function of time. Biodegradable polymers continue to degrade until polymer chains are small enough to dissolve in water and/or engage in the body metabolism.

Biodegradable balloon implants are vulnerable at relatively weak points compared to the overall strength of the balloon surface. Cracks generally begin to form at the weak points before polymeric matrix degradation. These cracks eventually cause implant failure and loss of functionality even before reduction of mechanical properties in the polymeric system.

SUMMARY

In some applications, a balloon implantation kit is provided that includes an inflatable biodegradable balloon configured to be implanted in a human body, and a container, which includes a hydrogel composition, which is configured to be introduced into the biodegradable balloon. For some applications, the biodegradable balloon includes a joint spacer for treatment of a joint of a human subject, such as a subacromial spacer, a glenohumeral spacer, or a spacer for another joint, such as a knee, hip, ankle, or hand (e.g., CMC1) joint. In these applications, the biodegradable balloon is configured to be inserted into a space of a joint of the human body, and is shaped to provide mechanical support to the joint until the biodegradable balloon resorbs into the human body. For other applications, the biodegradable balloon includes a soft tissue spacer.

Typically, the hydrogel composition is configured, upon formation of a breach through a wall of the biodegradable balloon after partial biodegradation but before complete biodegradation of the biodegradable balloon in the human body (after implantation), to leak through the breach at a rate less than that of normal saline. As a result, the biodegradable balloon remains inflated longer than it would if inflated with normal saline, as is conventional, rather than the hydrogel composition. For example, inflating the biodegradable balloon with the hydrogel composition may result in the balloon remaining inflated until biodegradation of the balloon, such as several weeks or months longer than if the balloon were instead inflated with normal saline. Even before the balloon biodegrades in the human body, one or more breaches may form through the wall of the balloon because of the mechanical forces applied to the balloon by the human body, e.g., by the joint in which the balloon is implanted.

For some applications, the hydrogel composition is configured, upon formation of the breach through the wall of the biodegradable balloon after partial biodegradation but before complete biodegradation of the biodegradable balloon in the human body, to react with a constituent of the human body so as to at least partially seal the breach.

For some of these applications, the hydrogel composition includes a hydrogel precursor, which is configured, upon formation of the breach, to react with the constituent of the human body so as to produce a hydrogel that at least partially seals the breach. For some applications, the hydrogel precursor includes gelatin or carboxylic acid, e.g., alginate, such as sodium alginate. For other applications, the hydrogel precursor includes hyaluronic acid.

For some applications, the hydrogel precursor is configured, upon formation of the breach, to chemically react with the constituent of the human body so as to become crosslinked to produce the hydrogel. For some of these applications, the constituent of the human body includes one or more enzymes, and the hydrogel precursor is configured to become crosslinked upon reacting with the one or more enzymes. Alternatively or additionally, for some of these applications, the constituent of the human body includes multivalent metal ions (e.g. divalent or trivalent ions), and the hydrogel precursor is configured to become crosslinked upon reacting with the multivalent metal ions. For example, the multivalent metal may include calcium ions, magnesium ions, iron ions, or a combination thereof. Alternatively or additionally, for some of these applications, the constituent of the human body includes one or more polysaccharides, and the hydrogel precursor is configured to become crosslinked upon reacting with the one or more polysaccharides.

For some of these applications, the hydrogel precursor is configured to become crosslinked upon a change in pH of the hydrogel precursor that occurs upon contact with the constituent of the human body. For example, the hydrogel precursor may include chitosan, such as chitosan acetate solution. For some applications, the hydrogel precursor has a pH less than 7.2, and is configured to become crosslinked at a pH of 7.4 upon contact with the constituent of the human body.

For some of these applications, the constituent of the human body includes proteins, and the hydrogel precursor is configured to become crosslinked upon a click chemistry reaction with the proteins. For example, the hydrogel precursor may include oxidized dextran solution, which is configured to become crosslinked upon a click chemistry reaction with amines of the proteins of the constituent of the human body.

For some applications, the hydrogel composition includes a hydrogel, which is configured, upon formation of the breach, to react with the constituent of the human body so as to further gel so as to at least partially seal the breach. For some of these applications, the hydrogel, before formation of the breach, is not crosslinked, and is configured, upon formation of the breach, to react with the constituent of the human body so as to further gel by becoming crosslinked; alternatively, the hydrogel, before formation of the breach, is crosslinked, and is configured, upon formation of the breach, to react with the constituent of the human body so as to further gel by becoming further crosslinked. For example, the hydrogel may include hyaluronic acid. For some applications, the hydrogel is configured, upon being pressurized during injection of the hydrogel into the biodegradable balloon, to become less viscous than when in the container.

For some applications, the hydrogel composition includes a hydrogel precursor, which is configured, after introduction of the hydrogel composition into the biodegradable balloon in the human body, to form a hydrogel in the biodegradable balloon while the wall of the biodegradable balloon is fully intact. Typically, the hydrogel composition forms the hydrogel soon after introduction into the biodegradable balloon in the human body. The relatively high viscosity of the hydrogel prevents or reduces leakage of the hydrogel through any breaches that form through the wall of the biodegradable balloon after partial biodegradation but before complete biodegradation of the biodegradable balloon in the human body (after implantation). In addition, leakage of the hydrogel may be at least partially blocked by contact with tissue of the human body adjacent to the balloon. For some of these applications, the hydrogel precursor is configured to form the hydrogel by becoming crosslinked.

For some of these applications, the hydrogel precursor includes a thermoresponsive polymer that is liquid (i.e., a running liquid) at less than a gelling temperature and forms the hydrogel at greater than the gelling temperature, the gelling temperature having a value of between 30 and 37 degrees C. (e.g., at human body temperature). For example, the thermoresponsive polymer may include a block copolymer of (a) polyethylene glycol and (b) at least one chemical compound selected from the group consisting of: lactic acid, glycolic acid, and caprolactone (e.g., a mixture or copolymer of two or more of these chemical compounds). Such block copolymers are known to biodegrade and be eliminated from the body. For others of these applications, the hydrogel precursor includes at least one of (a) alginate and a calcium salt, (b) hyaluronic acid, and (c) gelatin.

For some applications, the hydrogel composition includes a hydrogel, already when in the container. For example, the hydrogel may include hyaluronic acid, such as crosslinked hyaluronic acid. For some applications, the hydrogel is configured, upon being pressurized during injection of the hydrogel into the biodegradable balloon, to become less viscous than when in the container.

There is therefore provided, apparatus including a balloon implantation kit, which includes:

an inflatable biodegradable balloon, which is configured to be implanted in a human body; and a container, which includes a hydrogel composition, which is configured to be introduced into the biodegradable balloon.

For some applications, the hydrogel composition is configured, upon formation of a breach through a wall of the biodegradable balloon after partial biodegradation but before complete biodegradation of the biodegradable balloon in the human body, to leak through the breach at a rate less than that of normal saline.

For some applications, the hydrogel composition includes a solution.

For some applications, the hydrogel composition includes a dispersion.

For some applications, the hydrogel composition is configured, upon formation of a breach through a wall of the biodegradable balloon after partial biodegradation but before complete biodegradation of the biodegradable balloon in the human body, to react with a constituent of the human body so as to at least partially occlude the breach.

For some applications, the hydrogel composition includes a hydrogel precursor, which is configured, upon formation of the breach, to react with the constituent of the human body so as to produce a hydrogel that at least partially occludes the breach.

For some applications, the hydrogel precursor is configured to produce the hydrogel upon a change in pH of the hydrogel precursor that occurs upon contact with the constituent of the human body.

For some applications, the hydrogel composition is liquid before introduction into the biodegradable balloon.

For some applications, the hydrogel precursor includes carboxylic acid.

For some applications, the hydrogel precursor includes alginate.

For some applications, the hydrogel precursor includes sodium alginate.

For some applications, the hydrogel precursor includes hyaluronic acid.

For some applications, the hydrogel precursor is configured, upon formation of the breach, to chemically react with the constituent of the human body so as to become crosslinked to produce the hydrogel. For some applications, the constituent of the human body includes one or more enzymes, and the hydrogel precursor is configured to become crosslinked upon reacting with the one or more enzymes. For some applications, the constituent of the human body includes multivalent metal ions, and the hydrogel precursor is configured to become crosslinked upon reacting with the multivalent metal ions. For some applications, the multivalent metal ions include metal ions selected from the group consisting of: calcium ions, magnesium ions, and iron ions. For some applications, the constituent of the human body includes one or more polysaccharides, and the hydrogel precursor is configured to become crosslinked upon reacting with the one or more polysaccharides.

For some applications, the hydrogel precursor is configured to become crosslinked upon a change in pH of the hydrogel precursor that occurs upon contact with the constituent of the human body.

For some applications, the hydrogel precursor includes chitosan.

For some applications, the hydrogel precursor includes chitosan acetate solution.

For some applications, the hydrogel precursor has a pH less than 7.2, and is configured to become crosslinked at a pH of 7.4 upon contact with the constituent of the human body.

For some applications, the constituent of the human body includes proteins, and the hydrogel precursor is configured to become crosslinked upon a click chemistry reaction with the proteins.

For some applications, the hydrogel precursor includes oxidized dextran solution, which is configured to become crosslinked upon a click chemistry reaction with amines of the proteins of the constituent of the human body.

For some applications, the hydrogel precursor is configured, upon formation of the breach, to physically react with the constituent of the human body so as to produce the hydrogel.

For some applications, the hydrogel composition includes a hydrogel, which is configured, upon formation of the breach, to react with the constituent of the human body so as to further gel so as to at least partially occlude the breach.

For some applications, the hydrogel, before formation of the breach, is not crosslinked, and is configured, upon formation of the breach, to react with the constituent of the human body so as to further gel by becoming crosslinked.

For some applications, the hydrogel includes hyaluronic acid.

For some applications, the hydrogel is configured to become less viscous upon being pressurized during injection of the hydrogel into the biodegradable balloon.

For some applications, the hydrogel composition includes a hydrogel precursor, which is configured, after introduction of the hydrogel composition into the biodegradable balloon in the human body, to form a hydrogel in the biodegradable balloon while a wall of the iodegradable balloon is fully intact.

For some applications, the hydrogel precursor is configured to form the hydrogel by becoming crosslinked.

For some applications, the hydrogel precursor includes a thermoresponsive polymer that is liquid at less than a gelling temperature and forms the hydrogel at greater than the gelling temperature, the gelling temperature having a value of between 30 and 37 degrees C.

For some applications, the thermoresponsive polymer includes a block copolymer of (a) polyethylene glycol and (b) at least one chemical compound selected from the group consisting of: lactic acid, glycolic acid, and caprolactone.

For some applications, the thermoresponsive polymer includes a PLGA-PEG-PLGA triblock copolymer of poly(lactic-co-glycolic acid) (PLGA) and ployethylene gycol (PEG).

For some applications, the hydrogel precursor includes alginate and a calcium salt.

For some applications, the hydrogel precursor includes hyaluronic acid.

For some applications, the hydrogel composition includes a hydrogel.

For some applications, the hydrogel includes hyaluronic acid.

For some applications, the hydrogel includes crosslinked hyaluronic acid.

For some applications, the hydrogel is configured to become less viscous upon being pressurized during injection of the hydrogel into the biodegradable balloon.

For some applications, the biodegradable balloon has a volume of between 1 and 300 ml when fully inflated.

For some applications, the biodegradable balloon is configured to be inserted into a space of a joint of the human body, and is shaped to provide mechanical support to the joint until the biodegradable balloon resorbs into the human body.

For some applications, the biodegradable balloon has an average wall thickness of between 25 and 400 microns.

For some applications, the balloon implantation kit further includes a delivery sheath in which the biodegradable balloon is removably disposed.

For some applications, the balloon implantation kit further includes an inflation rod, which is removably coupled in fluid communication with an interior of the biodegradable balloon, and which has a length of at least 4 cm.

For some applications, the balloon implantation kit further includes sterile packaging in which the biodegradable balloon is removably packaged in a sterile state.

There is further provided, apparatus including a balloon implantation kit, which includes:

an inflatable biodegradable balloon, which is configured to be implanted in a human body; and a hydrogel composition, which is contained within the biodegradable balloon.

For some applications, the hydrogel composition is configured, upon formation of a breach through a wall of the biodegradable balloon after partial biodegradation but before complete biodegradation of the biodegradable balloon in the human body, to leak through the breach at a rate less than that of normal saline.

For some applications, the hydrogel composition includes a solution.

For some applications, the hydrogel composition includes a dispersion.

For some applications, the hydrogel composition is configured, upon formation of a breach through a wall of the biodegradable balloon after partial biodegradation but before complete biodegradation of the biodegradable balloon in the human body, to react with a constituent of the human body so as to at least partially occlude the breach.

For some applications, the hydrogel composition includes a hydrogel precursor, which is configured, upon formation of the breach, to react with the constituent of the human body so as to produce a hydrogel that at least partially occludes the breach.

For some applications, the hydrogel precursor is configured to produce the hydrogel upon a change in pH of the hydrogel precursor that occurs upon contact with the constituent of the human body.

For some applications, the hydrogel composition is liquid before introduction into the biodegradable balloon.

For some applications, the hydrogel precursor includes carboxylic acid.

For some applications, the hydrogel precursor includes alginate.

For some applications, the hydrogel precursor includes sodium alginate.

For some applications, the hydrogel precursor includes hyaluronic acid.

For some applications, the hydrogel precursor is configured, upon formation of the breach, to chemically react with the constituent of the human body so as to become crosslinked to produce the hydrogel. For some applications, the constituent of the human body includes one or more enzymes, and the hydrogel precursor is configured to become crosslinked upon reacting with the one or more enzymes. For some applications, the constituent of the human body includes multivalent metal ions, and the hydrogel precursor is configured to become crosslinked upon reacting with the multivalent metal ions. For some applications, the multivalent metal ions include metal ions selected from the group consisting of: calcium ions, magnesium ions, and iron ions. For some applications, the constituent of the human body includes one or more polysaccharides, and the hydrogel precursor is configured to become crosslinked upon reacting with the one or more polysaccharides.

For some applications, the hydrogel precursor is configured to become crosslinked upon a change in pH of the hydrogel precursor that occurs upon contact with the constituent of the human body.

For some applications, the hydrogel precursor includes chitosan.

For some applications, the hydrogel precursor includes chitosan acetate solution.

For some applications, the hydrogel precursor has a pH less than 7.2, and is configured to become crosslinked at a pH of 7.4 upon contact with the constituent of the human body.

For some applications, the constituent of the human body includes proteins, and the hydrogel precursor is configured to become crosslinked upon a click chemistry reaction with the proteins.

For some applications, the hydrogel precursor includes oxidized dextran solution, which is configured to become crosslinked upon a click chemistry reaction with amines of the proteins of the constituent of the human body.

For some applications, the hydrogel precursor is configured, upon formation of the breach, to physically react with the constituent of the human body so as to produce the hydrogel.

For some applications, the hydrogel composition includes a hydrogel, which is configured, upon formation of the breach, to react with the constituent of the human body so as to further gel so as to at least partially occlude the breach.

For some applications, the hydrogel, before formation of the breach, is not crosslinked, and is configured, upon formation of the breach, to react with the constituent of the human body so as to further gel by becoming crosslinked.

For some applications, the hydrogel includes hyaluronic acid.

For some applications, the hydrogel is configured to become less viscous upon being pressurized during injection of the hydrogel into the biodegradable balloon.

For some applications, the hydrogel composition includes a hydrogel precursor, which is configured, after introduction of the hydrogel composition into the biodegradable balloon in the human body, to form a hydrogel in the biodegradable balloon while a wall of the biodegradable balloon is fully intact.

For some applications, the hydrogel precursor is configured to form the hydrogel by becoming crosslinked.

For some applications, the hydrogel precursor includes a thermoresponsive polymer that is liquid at less than a gelling temperature and forms the hydrogel at greater than the gelling temperature, the gelling temperature having a value of between 30 and 37 degrees C.

For some applications, the thermoresponsive polymer includes a block copolymer of (a) polyethylene glycol and (b) at least one chemical compound selected from the group consisting of: lactic acid, glycolic acid, and caprolactone.

For some applications, the thermoresponsive polymer includes a PLGA-PEG-PLGA triblock copolymer.

For some applications, the hydrogel precursor includes alginate and a calcium salt.

For some applications, the hydrogel precursor includes hyaluronic acid.

For some applications, the hydrogel composition includes a hydrogel.

For some applications, the hydrogel includes hyaluronic acid.

For some applications, the hydrogel includes crosslinked hyaluronic acid.

For some applications, the hydrogel is configured to become less viscous upon being pressurized during injection of the hydrogel into the biodegradable balloon.

For some applications, the biodegradable balloon has a volume of between 1 and 300 ml when fully inflated.

For some applications, the biodegradable balloon is configured to be inserted into a space of a joint of the human body, and is shaped to provide mechanical support to the joint until the biodegradable balloon resorbs into the human body.

For some applications, the biodegradable balloon has an average wall thickness of between 25 and 400 microns.

For some applications, the balloon implantation kit further includes a delivery sheath in which the biodegradable balloon is removably disposed.

For some applications, the balloon implantation kit further includes an inflation rod, which is removably coupled in fluid communication with an interior of the biodegradable balloon, and which has a length of at least 4 cm.

For some applications, the balloon implantation kit further includes sterile packaging in which the biodegradable balloon is removably packaged in a sterile state.

There is still further provided, apparatus including a balloon implantation kit, which includes:

an inflatable biodegradable balloon configured to be implanted in a human body; and a container, which includes a viscous composition, which is configured to be injected into the biodegradable balloon, and, upon being pressurized during injection into the biodegradable balloon, to become less viscous than when in the container.

For some applications, the viscous composition includes a hydrogel composition.

There is additionally provided, a method including:

implanting, in a human body, an inflatable biodegradable balloon of a balloon implantation kit; and thereafter, introducing, from a container of the balloon implantation kit, a hydrogel composition into the biodegradable balloon.

For some applications, the hydrogel composition is configured, upon formation of a breach through a wall of the biodegradable balloon after partial biodegradation but before complete biodegradation of the biodegradable balloon in the human body, to leak through the breach at a rate less than that of normal saline.

For some applications, the hydrogel composition includes a solution.

For some applications, the hydrogel composition includes a dispersion.

For some applications, the hydrogel composition is configured, upon formation of a breach through a wall of the biodegradable balloon after partial biodegradation but before complete biodegradation of the biodegradable balloon in the human body, to react with a constituent of the human body so as to at least partially occlude the breach.

For some applications:

the hydrogel composition includes a hydrogel precursor, which is configured, upon formation of the breach, to react with the constituent of the human body so as to produce a hydrogel that at least partially occludes the breach, and introducing the hydrogel composition into the biodegradable balloon includes introducing the hydrogel precursor into the biodegradable balloon.

For some applications, the hydrogel precursor is configured to produce the hydrogel upon a change in pH of the hydrogel precursor that occurs upon contact with the constituent of the human body.

For some applications:

the hydrogel composition is liquid before introduction into the biodegradable balloon, and introducing the hydrogel precursor into the biodegradable balloon includes introducing the liquid hydrogel precursor into the biodegradable balloon.

For some applications, the hydrogel precursor includes carboxylic acid.

For some applications, the hydrogel precursor includes alginate.

For some applications, the hydrogel precursor includes sodium alginate.

For some applications, the hydrogel precursor includes hyaluronic acid.

For some applications, the hydrogel precursor is configured, upon formation of the breach, to chemically react with the constituent of the human body so as to become crosslinked to produce the hydrogel.

For some applications, the constituent of the human body includes one or more enzymes, and the hydrogel precursor is configured to become crosslinked upon reacting with the one or more enzymes.

For some applications, the constituent of the human body includes multivalent metal ions, and the hydrogel precursor is configured to become crosslinked upon reacting with the multivalent metal ions.

For some applications, the multivalent metal ions include metal ions selected from the group consisting of: calcium ions, magnesium ions, and iron ions.

For some applications, the constituent of the human body includes one or more polysaccharides, and the hydrogel precursor is configured to become crosslinked upon reacting with the one or more polysaccharides.

For some applications, the hydrogel precursor is configured to become crosslinked upon a change in pH of the hydrogel precursor that occurs upon contact with the constituent of the human body.

For some applications, the hydrogel precursor includes chitosan.

For some applications, the hydrogel precursor includes chitosan acetate solution.

For some applications, the hydrogel precursor has a pH less than 7.2, and is configured to become crosslinked at a pH of 7.4 upon contact with the constituent of the human body.

For some applications, the constituent of the human body includes proteins, and the hydrogel precursor is configured to become crosslinked upon a click chemistry reaction with the proteins.

For some applications, the hydrogel precursor includes oxidized dextran solution, which is configured to become crosslinked upon a click chemistry reaction with amines of the proteins of the constituent of the human body.

For some applications, the hydrogel precursor is configured, upon formation of the breach, to physically react with the constituent of the human body so as to produce the hydrogel.

For some applications:

the hydrogel composition includes a hydrogel, which is configured, upon formation of the breach, to react with the constituent of the human body so as to further gel so as to at least partially occlude the breach, and introducing the hydrogel composition into the biodegradable balloon includes introducing the hydrogel into the biodegradable balloon.

For some applications, the hydrogel, before formation of the breach, is not crosslinked, and is configured, upon formation of the breach, to react with the constituent of the human body so as to further gel by becoming crosslinked.

For some applications, the hydrogel includes hyaluronic acid.

For some applications:

the hydrogel is configured to become less viscous upon being pressurized during injection of the hydrogel into the biodegradable balloon, and introducing the hydrogel into the biodegradable balloon includes pressurizing the hydrogel during injection of the hydrogel into the biodegradable balloon.

For some applications:

the hydrogel composition includes a hydrogel precursor, which is configured, after introduction of the hydrogel composition into the biodegradable balloon in the human body, to form a hydrogel in the biodegradable balloon while a wall of the biodegradable balloon is fully intact, and introducing the hydrogel composition into the biodegradable balloon includes introducing the hydrogel precursor into the biodegradable balloon.

For some applications, the hydrogel precursor is configured to form the hydrogel by becoming crosslinked.

For some applications, the hydrogel precursor includes a thermoresponsive polymer that is liquid at less than a gelling temperature and forms the hydrogel at greater than the gelling temperature, the gelling temperature having a value of between 30 and 37 degrees C.

For some applications, the thermoresponsive polymer includes a block copolymer of (a) polyethylene glycol and (b) at least one chemical compound selected from the group consisting of: lactic acid, glycolic acid, and caprolactone.

For some applications, the thermoresponsive polymer includes a PLGA-PEG-PLGA triblock copolymer.

For some applications, the hydrogel precursor includes alginate and a calcium salt.

For some applications, the hydrogel precursor includes hyaluronic acid.

For some applications:

the hydrogel composition includes a hydrogel, and introducing the hydrogel composition into the biodegradable balloon includes introducing the hydrogel into the biodegradable balloon.

For some applications, the hydrogel includes hyaluronic acid.

For some applications, the hydrogel includes crosslinked hyaluronic acid.

For some applications:

the hydrogel is configured to become less viscous upon being pressurized during injection of the hydrogel into the biodegradable balloon, and introducing the hydrogel into the biodegradable balloon includes pressurizing the hydrogel during injection of the hydrogel into the biodegradable balloon.

For some applications, the biodegradable balloon has a volume of between 1 and 300 ml when fully inflated.

For some applications, implanting the biodegradable balloon includes inserting the biodegradable balloon into a space of a joint of the human body, and the biodegradable balloon is shaped to provide mechanical support to the joint until the biodegradable balloon resorbs into the human body.

For some applications, the biodegradable balloon has an average wall thickness of between 25 and 400 microns.

For some applications, implanting the biodegradable balloon includes inserting, into the human body, a delivery sheath of the balloon implantation kit, and the biodegradable balloon is removably disposed in the delivery sheath.

For some applications, introducing the hydrogel composition into the biodegradable balloon includes introducing the hydrogel composition through an inflation rod of the balloon implantation kit, the inflation rod is removably coupled in fluid communication with an interior of the biodegradable balloon, and the inflation rod has a length of at least 4 cm.

For some applications, the balloon implantation kit further includes sterile packaging in which the biodegradable balloon is removably packaged in a sterile state.

There is yet additionally provided, a method including:
implanting, in a human body, an inflatable biodegradable balloon of a balloon implantation kit; and
thereafter, injecting, from a container, a viscous composition into the biodegradable balloon,
wherein injecting includes pressurizing the viscous composition such that the viscous composition becomes less viscous than when in the container.

For some applications, the viscous composition includes a hydrogel composition.

The present disclosure will be more fully understood from the following detailed description thereof, taken together with the drawings, in which:

BRIEF DESCRIPTION OF THE DRAWINGS

FIG. 2D is a schematic illustration of the formation of a breach through a wall of a biodegradable balloon.

DETAILED DESCRIPTION

Figure 1A:
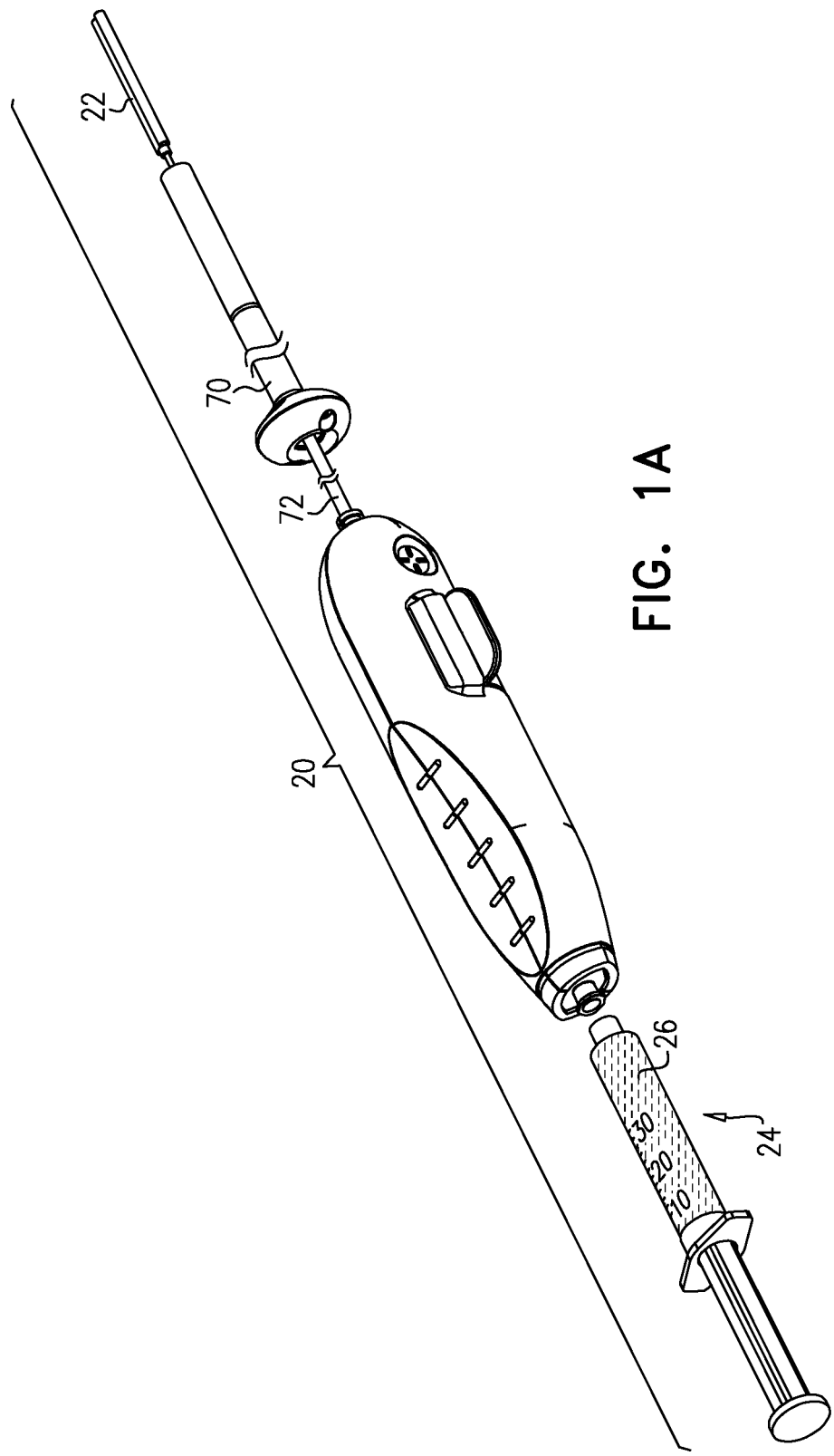
FIGS. 1A-B are schematic illustrations of a balloon implantation kit.
Figure 1B:
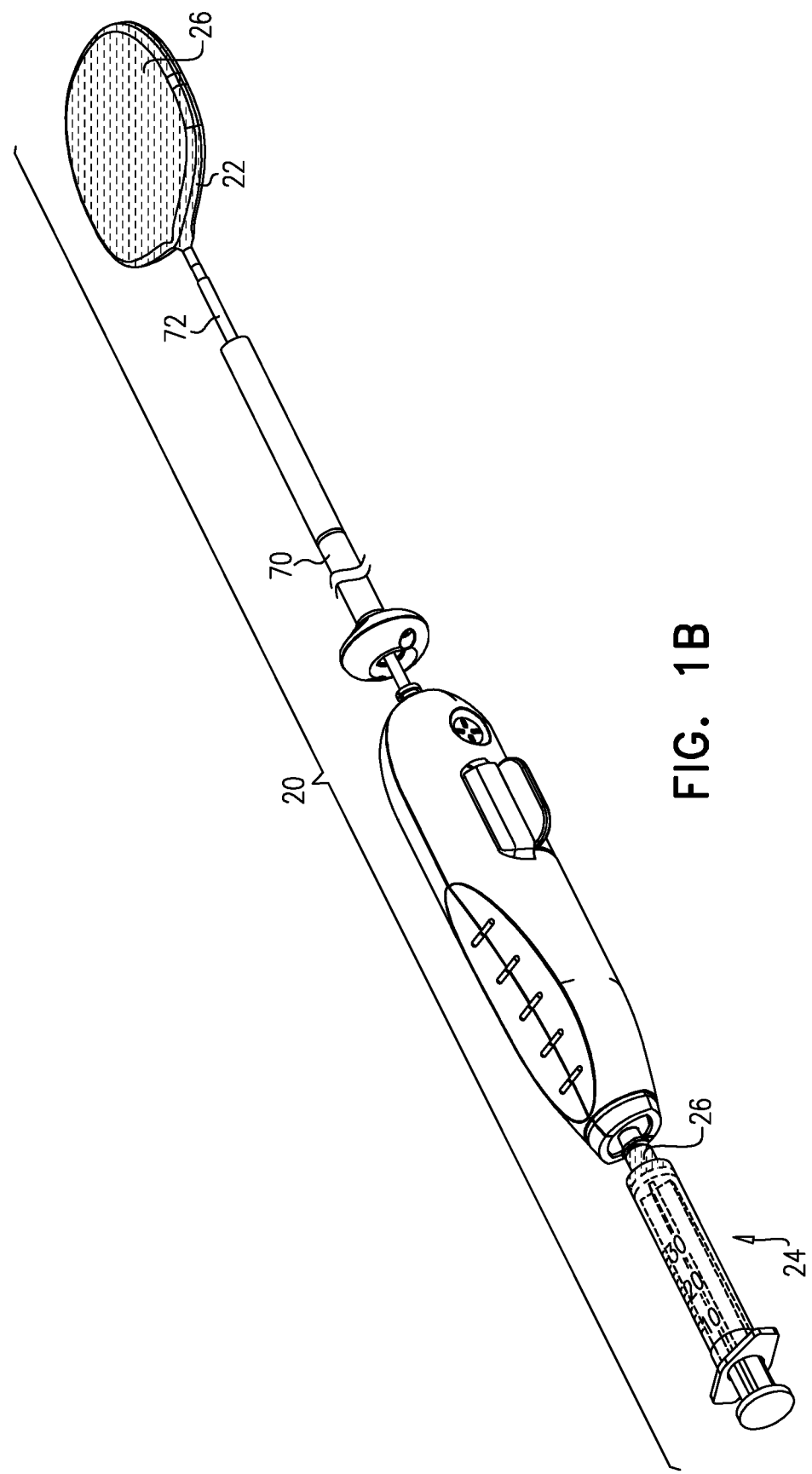

FIGS. 1A-B are schematic illustrations of balloon implantation kit 20. Balloon implantation kit 20 includes an inflatable biodegradable balloon 22 configured to be implanted in a human body, and a container 24, which includes a hydrogel composition 26, which is configured to be introduced into biodegradable balloon 22. For example, hydrogel composition 26 may include a solution or a dispersion. FIG. 1A shows biodegradable balloon 22 before inflation with hydrogel composition 26, while hydrogel composition is in container 24. FIG. 1B shows biodegradable balloon 22 after the balloon has been inflated with hydrogel composition 26. For some applications, container 24 includes a syringe, such as a conventional syringe. For illustrative purposes, biodegradable balloon 22 is shown as transparent, but this is not necessarily the case.

For some applications, biodegradable balloon 22 includes a joint spacer for treatment of a joint of a human subject, such as a subacromial spacer, a glenohumeral spacer, or a spacer for another joint, such as a knee, hip, ankle, or hand (e.g., CMC1) joint. In these applications, biodegradable balloon 22 is configured to be inserted into a space of a joint of the human body, and is shaped to provide mechanical support to the joint until biodegradable balloon 22 resorbs into the human body. The joint spacer may implement techniques described in the patents and patent application publications incorporated by reference hereinbelow. The joint spacer may be deployed using techniques described hereinbelow with reference to FIGS. 2A-C. For other applications, biodegradable balloon 22 may include a hydrophilic osmotic hydrogel expander, an intra-gastric balloon, e.g., for patients suffering from obesity, a minimally-invasive antral membrane balloon, a micro-balloon for intrinsic sphincter deficiency, a balloon for implantation in the prostate, or a soft tissue spacer.

For some applications, balloon implantation kit 20 further includes sterile packaging in which biodegradable balloon 22 is removably packaged in a sterile state.

Optionally, balloon implantation kit 20 includes a plurality of biodegradable balloons 22, for example having different sizes and/or shapes. Typically, biodegradable balloon 22 is semi-compliant to elastic, although it may alternatively be substantially non-compliant.

Even before balloon 22 biodegrades in the human body, one or more breaches 30 may form through wall 32 of balloon 22 because of the mechanical forces applied to the balloon by the human body, e.g., by the joint in which the balloon is implanted. Such mechanical forces typically range from a few newtons to hundreds of newtons. Breach 30 may be any opening through wall 32 of biodegradable balloon 22, such as a hole or a crack, e.g., a micro-crack. Typically, hydrogel composition 26 is configured, upon formation of a breach 30 through a wall 32 of biodegradable balloon 22 after partial biodegradation but before complete biodegradation of biodegradable balloon 22 in the human body (after implantation), such as described hereinbelow with reference to FIG. 2D, to leak through breach 30 at a rate less than that of normal saline. As a result, biodegradable balloon 22 remains inflated longer than it would if inflated with normal saline, as is known in the art, rather than hydrogel composition 26. For example, inflating biodegradable balloon 22 with hydrogel composition 26 may result in the balloon remaining inflated until biodegradation of biodegradable balloon 22, such as several weeks or months longer than if the balloon were instead inflated with normal saline.

For some applications, biodegradable balloon 22 includes a polymer, which, for example, may be crystalline or semi-crystalline. For example, the polymer may include 3:1 Poly(L-lactide-co-ε-caprolactone). Balloons comprising this polymer with an average wall thickness of 100 microns generally remain inflated for eight weeks before breaches (e.g., cracks and holes) start to form as partial biodegradation occurs. These breaches result in the collapse of the balloon due to depletion of the inner solution by leakage through the formed breaches. Use of hydrogel composition 26 described herein generally prevents the leakage through the breaches, resulting in an extension of balloon inflation, such as for an additional few weeks or months.

As used in the present application, including in the claims, "biodegradable" means able to be broken down and absorbed or eliminated by the human body. For applications in which biodegradable balloon 22 includes a polymer, the biodegradation typically occurs because of four major mechanisms: hydrolysis (reaction with water in tissues), oxidation (due to oxidants produced by tissues), enzymatic degradation, and physical erosion.

For some applications, biodegradable balloon 22 has a volume of between 1 and 300 ml when fully inflated, such as between 9 and 11 ml, between 14 and 16 ml, between 23 and 26 ml, or between 50 and 60 ml. For some applications, biodegradable balloon 22 has an average wall thickness of between 25 and 400 microns, e.g., 100 microns.

For some applications, hydrogel composition 26 includes a biocompatible biodegradable polymer.

Delayed Gelling Configurations

For some applications, hydrogel composition 26 is configured, upon formation of breach 30 through wall 32 of biodegradable balloon 22 after partial biodegradation but before complete biodegradation of biodegradable balloon 22 in the human body, to react with a constituent of the human body so as to at least partially seal breach 30. Before at least partially sealing breach 30, hydrogel composition 26 may come into contact with the human body constituent either because hydrogel composition 26 slightly leaks out of balloon 22 and/or the constituent of the human body slightly leaks into balloon 22. Typically, the at least partial occlusion of breach 30 is due to mechanical interaction, rather than chemical interaction, of hydrogel composition 26 with wall 32 of biodegradable balloon 22.

For some of these applications, hydrogel composition 26 includes a hydrogel precursor, which is configured, upon formation of breach 30, to react with the constituent of the human body so as to produce a hydrogel that at least partially seals breach 30. As used in the present application, including in the claims, a "hydrogel" is a network of polymer chains that are hydrophilic, which exhibits no flow when in the steady-state; the polymer chains may or may not be chemically crosslinked. A "hydrogel" may be flexible or rigid, and semi-solid or solid. For some applications, hydrogel composition 26 is liquid when in container 24 before introduction into biodegradable balloon 22.

For some of these applications, the hydrogel precursor is configured to produce the hydrogel upon a change in pH of the solution surrounding the hydrogel precursor that occurs upon contact with the constituent of the human body. For example, the configuration and/or structure of the hydrogel precursor may change upon the change in pH. The pH change may modify some of the internal functional groups in the hydrogel precursor such that they can react immediately with other functional groups and form hydrogels.

For some applications, the hydrogel precursor includes carboxylic acid, e.g., includes alginate, such as sodium alginate. In an experiment conducted by the inventors, different alginate solutions in concentrations of 0.1%, 0.5%, 1%, 2%, and 3% w/v were prepared by dissolving sodium alginate in double distilled water or 0.9% NaCl Saline solution (pH adjusted to 7.4) while stirring for 30 minutes until complete dissolution occurred. The ability of alginate to crosslink in the presence of ionized calcium or human plasma was evaluated by adding alginate solution to calcium chloride or Human plasma solutions. Calcium chloride solutions were tested in concentrations of 1, 0.5. 0.4, 0.3, 0.2, 0.1, and 0.01 g/dL in distilled, de-ionized water (DDW). The alginate gels were prepared in a 12 wells plate, with each concentration in a different well. Calcium chloride (1 ml) was added to each well, and then 1 ml alginate solution was added to the wells. The solutions were manually mixed and the formation of the gel visually determined. The viscosity of alginate gels was performed using a Physica MCR 101 rheometer (Anton Paar GmbH, Austria) with a measuring plate type PP25 D=25mm. Three alginate gels with concentrations of 1%, 2%, and 3% w/v in DDW crosslinked with 0.2% calcium chloride were tested in duplicates.

The following experimental results were obtained:
  there was no significant change in crosslinking ability while dissolving alginate in DDW or 0.9% NaCl saline solution; in both media crosslinking occurred;
  the minimum concentration of calcium chloride required was 0.2 g/dL for 1%, 2%, and 3% alginate, and 0.1 g/dL for 2% and 3% alginate solution;
  in the rheology test, the samples showed the same behavior for each concentration;
  viscosity decreased as the shear rate or stirrer speed increased; and
  1% alginate solution mixed with 0.2% calcium chloride showed uniform gel, and the viscosity measurements demonstrated a gel with a high viscosity.

For some applications, the hydrogel precursor includes hyaluronic acid, which may interact with proteins and/or enzymes in the human body. Hyaluronic acid has the ability to crosslink with surface-bound collagen type II fibrils, to interact reversibly with albumin, and to crosslink and become complexed with the PRG4 molecule. It has been shown that injection of HA into the bursa causes pain relief due to crosslinking with collagen in rotator cuff syndrome patients—see Majd S E et al., "Both Hyaluronan and Collagen Type II Keep Proteoglycan 4 (Lubricin) at the Cartilage Surface in a Condition That Provides Low Friction during Boundary Lubrication," Langmuir 2014, 30, 14566-14572, which is incorporated herein by reference.

For some applications, the hydrogel precursor is configured, upon formation of breach 30, to chemically react with the constituent of the human body so as to become crosslinked to produce the hydrogel. For some of these applications, the constituent of the human body includes one or more enzymes, and the hydrogel precursor is configured to become crosslinked upon reacting with the one or more enzymes. Alternatively or additionally, for some of these applications, the constituent of the human body includes multivalent metal ions (e.g. divalent or trivalent ions), and the hydrogel precursor is configured to become crosslinked upon reacting with the multivalent metal ions. For example, the multivalent metal may include calcium ions, magnesium ions, iron ions, or a combination thereof. Alternatively or additionally, for some of these applications, the constituent of the human body includes one or more polysaccharides, and the hydrogel precursor is configured to become crosslinked upon reacting with the one or more polysaccharides.

For some applications, the hydrogel precursor includes L-Dopaquinone, embelic acid, potassium embelate, or 5-O-methyl embelin that crosslink collagen. Depending on the concentration and other conditions of the hydrogel precursor, it may become crosslinked either while the wall of biodegradable balloon 22 is fully intact, or only upon reacting with the constituent of the human body upon formation of breach 30.

For some of these applications, the hydrogel precursor is configured to become crosslinked upon a change in pH of the hydrogel precursor that occurs upon contact with the constituent of the human body. For example, the hydrogel precursor may include (a) chitosan, such as chitosan acetate solution, or (b) gelatin. The presence of amino groups in chitosan (pKa=6.5) results in pH-sensitive behavior. For some applications, the hydrogel precursor has a pH less than 7.2, and is configured to (a) become crosslinked at a pH of 7.4 upon contact with the constituent of the human body, (b) precipitate at a pH of 7.4 upon contact with the constituent of the human body (e.g., a light precipitation such that the polymers are still associated with water and not fully precipitated), or both (a) and (b). In an experiment, chitosan was dissolved in acidic double distilled water (2% V/V of acetic acid, pH=2.7) until complete dissolution occurred. Then the pH was adjusted to 6.5 by adding small quantities of 1N NaOH while stirring. A clear solution was obtained. Table 1 summarizes the tested chitosan concentrations:

TABLE 1

| | Chitosan [mg] | Solvent [ml] | Initial concentration [w/v %] | Volume of 1N NaOH added [ml] | Concentration after NaOH addition [w/v %] |
|---|---|---|---|---|---|
| 1 | 50.0 | 5 | 1 | 1.4 | 0.78 |
| 2 | 100.0 | 5 | 2 | 1.2 | 1.61 |
| 3 | 150.0 | 5 | 3 | 0.8 | 2.58 |

The solidification ability of chitosan in both phosphate buffer and human plasma was evaluated by adding phosphate buffer or human plasma into the chitosan during mixing. The chitosan gels were prepared in a 12 wells plate, with a different concentration in each well. 1 ml of phosphate buffer or human plasma was added to each well, and then 1 ml chitosan solution was added to the wells. The solutions were manually mixed and the formation of the gel visually determined. Acidic water (pH=2.7) was used to completely dissolve the chitosan. The addition of 1N NaOH was used to increase the pH up to 6.5, in which the chitosan is still soluble. The ability of chitosan to sediment and to form a gel due to pH change was tested using Phosphate Buffer Saline (PBS, pH=7.4) and human plasma solutions. The sedimentation of the chitosan was visually determined. The 3% chitosan obtained was very viscous and it was very difficult to mix the solution using a magnetic stirrer.

For some of these applications, the constituent of the human body includes proteins, and the hydrogel precursor is configured to become crosslinked (e.g., imine crosslinked) upon a click chemistry reaction with the proteins. For example, the hydrogel precursor may include oxidized dextran solution, which is configured to become crosslinked upon a click chemistry reaction with amines of the proteins of the constituent of the human body.

For some of these applications, the hydrogel precursor is configured, upon formation of breach 30, to physically react with the constituent of the human body so as to produce the hydrogel (for example, the hydrogel might form as a result of reorientations of polymer chains in a solution upon physical interaction with the constituent of the human body). For example, such a physical reaction may occur when the hydrogel precursor includes hyaluronic acid or gelatin, which physically reacts with proteins, enzymes, or both in the human body.

For some applications, hydrogel composition 26 includes a hydrogel, which is configured, upon formation of breach 30, to react with the constituent of the human body so as to further gel so as to at least partially seal breach 30. For some of these applications, the hydrogel, before formation of breach 30, is not crosslinked, and is configured, upon formation of breach 30, to react with the constituent of the human body so as to further gel by becoming crosslinked; alternatively, the hydrogel, before formation of breach 30, is crosslinked, and is configured, upon formation of breach 30, to react with the constituent of the human body so as to further gel by becoming further crosslinked. For example, the hydrogel may include hyaluronic acid. For some applications, the hydrogel is configured, upon being pressurized during injection of the hydrogel into biodegradable balloon 22, to become less viscous than when in container 24.

Early Gelling Configurations

For some applications, hydrogel composition 26 includes a hydrogel precursor, which is configured, after introduction of hydrogel composition 26 into biodegradable balloon 22 in the human body, to form a hydrogel in biodegradable balloon 22 while wall 32 of biodegradable balloon 22 is fully intact. Typically, hydrogel composition 26 forms the hydrogel soon after introduction into biodegradable balloon 22 in the human body, such as within five minutes of introduction. The relatively high viscosity of the hydrogel prevents or reduces leakage of the hydrogel through any breaches 30 that form through wall 32 of biodegradable balloon 22 after partial biodegradation but before complete biodegradation of biodegradable balloon 22 in the human body (after implantation). In addition, leakage of the hydrogel may be at least partially blocked by contact with tissue of the human body adjacent to the balloon. For some of these applications, the hydrogel precursor is configured to form the hydrogel by becoming crosslinked.

For some of these applications, the hydrogel precursor includes a thermoresponsive polymer that is liquid (i.e., a running liquid) at less than a gelling temperature and forms the hydrogel at greater than the gelling temperature, the gelling temperature having a value of between 30 and 37 degrees C. (e.g., at human body temperature). For some of these applications, the thermoresponsive polymer is configured to form the hydrogel at greater than the gelling temperature as a result of reorientations of polymer chains. For example, the thermoresponsive polymer may include a block copolymer of (a) polyethylene glycol and (b) at least one chemical compound selected from the group consisting of: lactic acid, glycolic acid, and caprolactone (e.g., a mixture or copolymer of two or more of these chemical compounds). Such block copolymers are known to biodegrade and be eliminated from the body. For example, the block copolymer may include (a) a PLGA-PEG-PLGA triblock copolymer, or (b) a triblock copolymer of DL-lactic acid, glycolic acid, caprolactone and trimethylene carbonate where the PEG is in the middle, for example: DL-PLA-PEG-DL-PLA or when the polyester block is in the middle, for example: PEG-DL-PLGA-PEG. Some suitable thermogelling biodegradable polymers are described in the following reviews: Bae at al., J. Mater. Chem. B, 2013, 1, 5371; Dou et al. Adv. Healthcare Mater. 2014, 3, 977-988; and Kondia et al. Molecules 2016, 21, 1580, all of which are incorporated herein by reference.

In an experiment, balloon stability after filling with block copolymer solutions was assessed. A 15% block polymer in saline, which forms a gel at body temperature, but remains a running liquid at temperatures between 10-30 degrees C., was injected into three balloons to fill the balloons at temperatures below their gelling point. The polymers gelled at body temperature. To ascertain the effectiveness of the gels in blocking breaches (cracks and holes) through the walls of the balloons, 1 cm long and 2 cm long cuts were made in the balloons, and 2 mm and 3 mm holes were punched in the balloons, and the balloons were filled with the gelling polymers. The balloons were then immersed in a water bath at 37 degrees C. with a 500 gram weight placed on the balloons. The balloons remain inflated for two weeks with no leaks through the holes or cuts.

For some of these applications, the hydrogel precursor includes alginate and a calcium salt. For example, container 24 may be provided with the alginate and calcium salt as dry powder, and water may be added to the container prior to introduction of hydrogel composition 26 into biodegradable balloon 22. When in the balloon, the alginate powder slowly dissolves and crosslinks with the calcium to form a stable gel. The strength of the gel can be adjusted by the alginate concentration and calcium salt ratio. Typically, the amount of alginate in the gel is in the range of 1-5% w/w and the amount of calcium salt is about 10% w/w per the alginate powder.

For some of these applications, the hydrogel precursor includes hyaluronic acid. The hyaluronic acid may be introduced into balloon 22 as a gelling material or mixed with a crosslinking agent (e.g., divinyl sulfone) shortly before introduction into the balloon.

For some applications, the hydrogel precursor includes an oxidized polysaccharide, such as oxidized dextran or arabinogalactan, mixed with an amine (e.g., a diamine or polyamine) that reacts with the aldehyde groups to form imide bonds. The oxidation occurs in water at room temperature, e.g., using potassium periodate as an oxidizing agent. The ratio of saccharide unit to periodate determines the degree of oxidation. The oxidized polysaccharide powder is mixed with ethylenediamine, spermidine, spermine, or chitosan and the mixed powder is dispersed in water and injected into the balloon where the powders are dissolved and crosslink via imine bonds to form the gel.

Pre-Gelled Configurations

For some applications, hydrogel composition 26 includes a hydrogel, already when in container 24. For example, the hydrogel may include hyaluronic acid, such as crosslinked hyaluronic acid. For some applications, the hydrogel is configured, upon being pressurized during injection of the hydrogel into biodegradable balloon 22, to become less viscous than when in container 24.

Other Viscous Compositions

For some applications, container 24 of balloon implantation kit 20 includes a viscous composition, which is not necessarily a hydrogel composition, and which is configured to be injected into biodegradable balloon 22, and, upon being pressurized during injection into biodegradable balloon 22, to become less viscous than when in container 24.

Exemplary Deployment Method

Figure 2A:
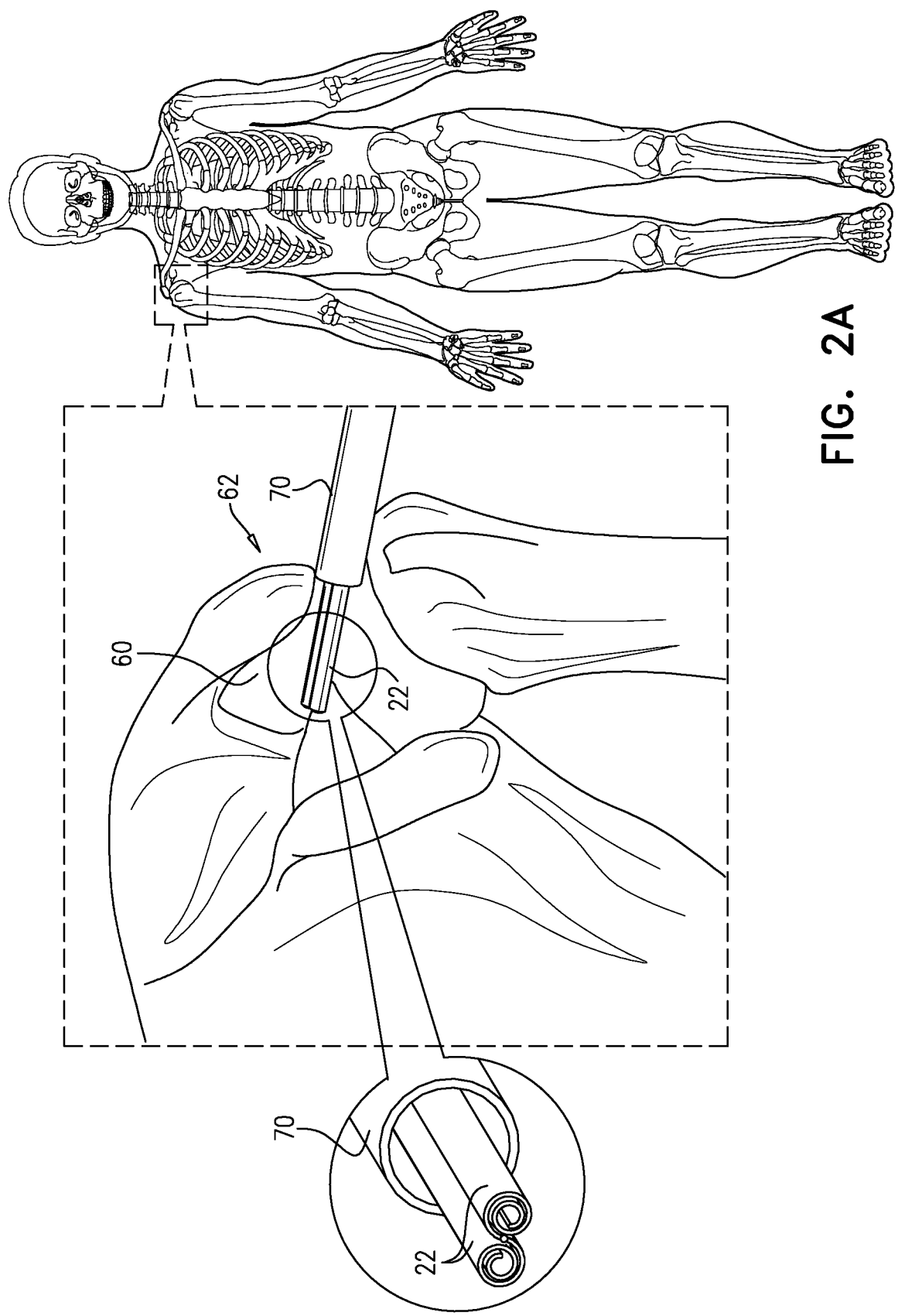
FIGS. 2A-C are schematic illustrations of a method of deploying a biodegradable balloon as a joint spacer into subacromial space of a shoulder joint.
Figure 2B:
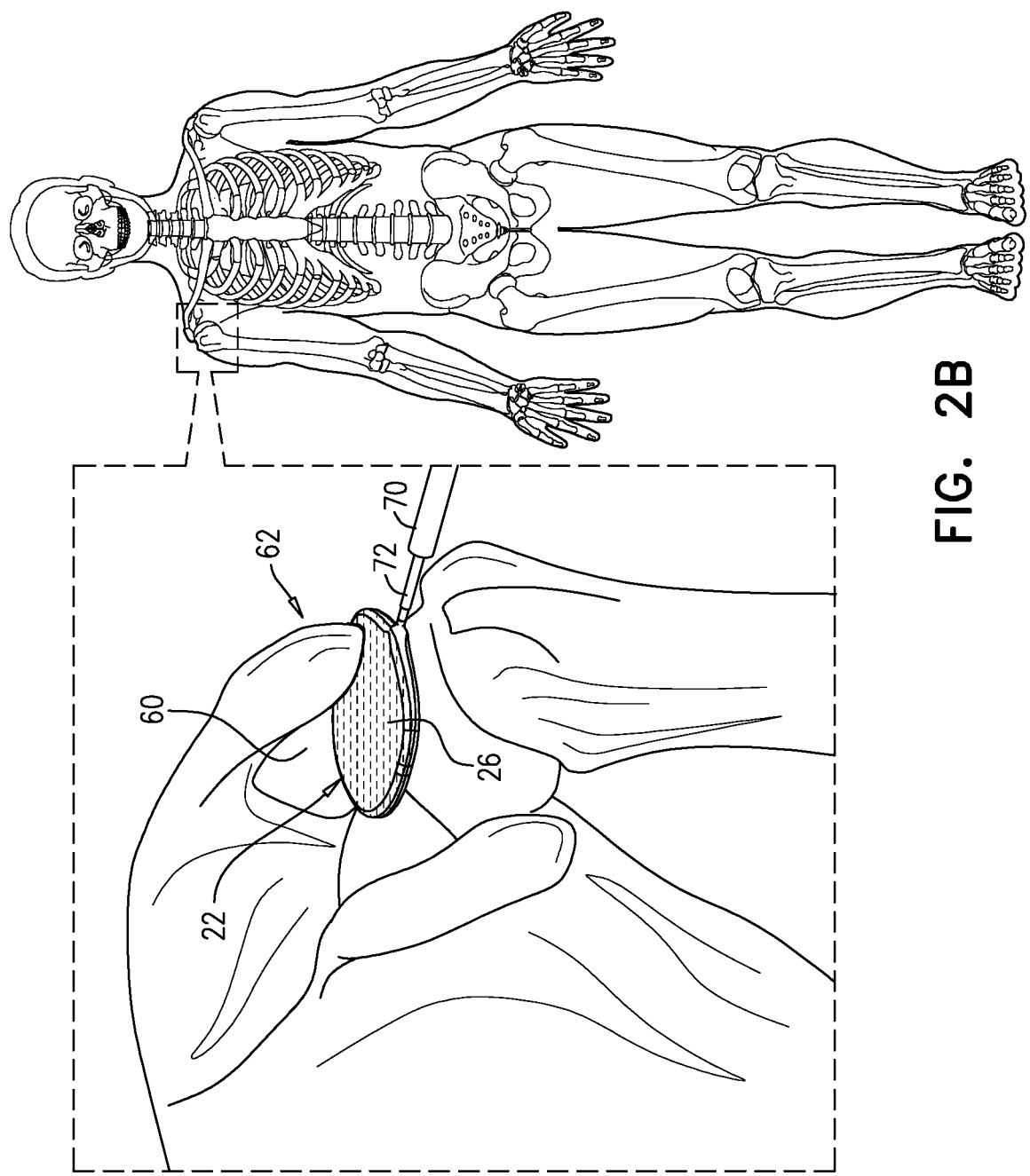
Figure 2C:
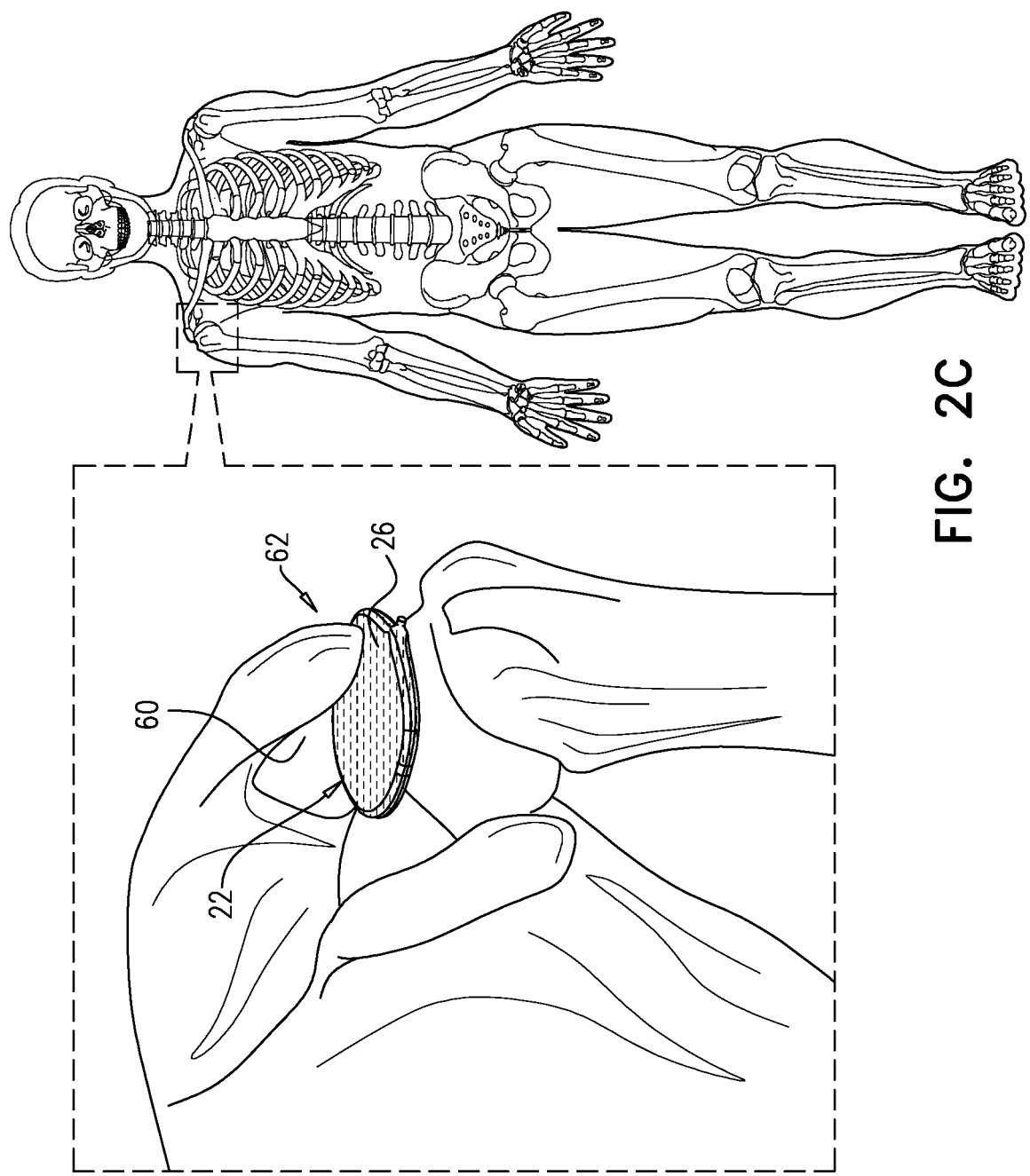

Reference is now made to FIGS. 2A-C, which are schematic illustrations of a method of deploying biodegradable balloon 22 as a joint spacer into subacromial space 60 of a shoulder joint 62. In the illustrated method, the joint spacer is a subacromial spacer; alternatively, the joint spacer is introduced into another joint and/or space, using this method mutatis mutandis.

As shown in FIG. 2A, biodegradable balloon 22 is arthroscopically inserted into subacromial space 60 while not inflated. Typically, this insertion is performed with biodegradable balloon 22 removably disposed in a delivery sheath 70, such as rolled or folded.

As shown in FIG. 2B, biodegradable balloon 22 is inflated with hydrogel composition 26 within the joint, such that biodegradable balloon 22 provides mechanical support to the joint until biodegradable balloon 22 resorbs into the body of the subject. For some applications, such as shown in FIG. 2B, balloon implantation kit 20 further includes an inflation rod 72, which is removably coupled in fluid communication with an interior of biodegradable balloon 22, and which typically has a length of at least 4 cm. Inflation rod 72 is used to introduce hydrogel composition 26 from container 24 into biodegradable balloon 22 after biodegradable balloon has been positioned in the joint (for example, container 24 may include a syringe, and may be coupled to inflation rod 72 as shown in FIG. 1B, described hereinabove).

As shown in FIG. 2C, inflation rod 72 is decoupled from biodegradable balloon 22, completing the implantation procedure.

Reference is made to FIG. 2D, which is a schematic illustration of the formation of a breach 30 through wall of biodegradable balloon 22. Sometimes, after implantation and inflation of biodegradable balloon 22 in the joint, and before biodegradation of the balloon, breach 30 forms through wall 32 of biodegradable balloon 22 because of mechanical forces applied to the balloon by the joint. Hydrogel composition 26 prevents or delays deflation of biodegradable balloon 22, using one or more of the techniques described hereinabove for at least partially sealing breach 30.

The scope of the present disclosure includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,753,390 to Shohat
U.S. Pat. No. 8,894,713 to Shohat et al.
PCT Publication WO 2008/111073 to Shohat
PCT Publication WO 2010/097724 to Shohat
PCT Publication WO 2012/017438 to Shohat et al.
PCT Publication WO 2013/057566 to Shohat It will be appreciated by persons skilled in the art that the present disclosure is not limited to what has been particularly shown and described hereinabove. Rather, the scope of the present disclosure includes both combinations and sub-combinations of the various features described hereinabove, as well as variations and modifications thereof that are not in the prior art, which would occur to persons skilled in the art upon reading the foregoing description.

What is claimed is:

1. An implant comprising:
an inflatable biodegradable balloon including a volume, a hydrogel composition, the hydrogel composition including a hydrogel precursor or a hydrogel, positioned in the volume,
wherein upon formation of a breach through a wall of the balloon when the balloon is implanted at a surgical site including a joint, the hydrogel composition is configured to leak through the breach at a rate less than that of normal saline and react with at least one constituent at the surgical site to at least partially occlude the breach, the breach being formed in the wall of the balloon before complete biodegradation of the balloon at the surgical site,
wherein the hydrogel composition reacting with the at least one constituent at the surgical site to at least partially occlude the breach provides for the inflatable biodegradable balloon to maintain mechanical support to the joint.

2. The implant of claim 1, wherein the hydrogel composition is a liquid before introduction into the volume.

3. The implant of claim 1, wherein the hydrogel precursor is configured to produce the hydrogel upon a change in pH of the hydrogel precursor upon contact with the constituent.

4. The implant of claim 1, wherein the hydrogel precursor is configured to chemically react with the constituent to become crosslinked to produce the hydrogel.

5. The implant of claim 4, wherein the constituent includes one or more enzymes, multivalent metal ions, polysaccharides, or proteins, wherein the hydrogel precursor is configured to become crosslinked upon reacting with the one or more enzymes, multivalent metal ions, polysaccharides, or proteins.

6. The implant of claim 5, wherein the multivalent metal ions include metal ions selected from the group consisting of: calcium ions, magnesium ions, and iron ions.

7. The implant of claim 4, wherein the hydrogel precursor is configured to become crosslinked upon a change in pH of the hydrogel precursor that occurs upon contact with the constituent.

8. The implant of claim 4, wherein the hydrogel precursor has a pH less than 7.2, and is configured to become crosslinked at a pH of 7.4 upon contact with the constituent.

9. The implant of claim 5, wherein the hydrogel precursor is configured to become crosslinked upon a click chemistry reaction with the proteins.

10. The implant of claim 9, wherein the hydrogel precursor comprises oxidized dextran solution configured to become crosslinked upon a click chemistry reaction with amines of the proteins of the constituent.

11. The implant of claim 1, wherein the hydrogel composition comprises a hydrogel configured, upon formation of the breach, to react with at least one constituent at the surgical site to further gel so as to at least partially occlude the breach.

12. The implant of claim 11, wherein the hydrogel is configured to become less viscous upon being pressurized during injection of the hydrogel into the volume.

13. The implant of claim 1, wherein the hydrogel composition comprises a solution.

14. The implant of claim 1, wherein the hydrogel composition comprises a dispersion.

15. The implant of claim 1, wherein the balloon is configured to be inserted into a space of a joint of a human body, and is shaped to provide mechanical support to the joint until the balloon resorbs into the human body.

16. A surgical kit comprising:
an inflatable biodegradable balloon configured to be implanted at a surgical site, and a container containing a hydrogel composition including a hydrogel precursor or a hydrogel to be introduced into the balloon,
wherein upon formation of a breach through a wall of the balloon when the balloon is inflated with the hydrogel composition and implanted at the surgical site including a joint, the hydrogel composition is configured to leak through the breach at a rate less than that of normal saline and react with at least one constituent at the surgical site to at least partially occlude the breach, the breach being formed in the wall of the balloon before complete biodegradation of the balloon at the surgical site,
wherein the hydrogel composition reacting with the at least one constituent at the surgical site to at least partially occlude the breach provides for the inflatable biodegradable balloon to maintain mechanical support to the joint.

17. The implant of claim 1, wherein the biodegradable balloon has a volume ranging from 1 to 300 ml when fully inflated.

18. The implant of claim 1, wherein the biodegradable balloon has an average wall thickness of ranging from 25 microns to 400 microns.

19. The kit of claim 16, wherein the hydrogel precursor is configured to produce the hydrogel upon a change in pH of the hydrogel precursor upon contact with the constituent.

20. The kit of claim 16, wherein the hydrogel precursor is configured to chemically react with the constituent to become crosslinked to produce the hydrogel.

* * * * *